United States Patent [19]
Reichel et al.

[11] 4,038,302
[45] July 26, 1977

[54] PROCESS FOR PREPARING 2-(CYCLOHEXENYL-4-)ETHYL-SILICON COMPOUNDS AND NOVEL PRODUCTS MADE THEREBY

[75] Inventors: Sigrid Reichel, Dresden; Rudolf Gottfried, Cossebaude near Dresden, both of Germany

[73] Assignee: VEB Chemiewerk Nuenchritz, Nuenchritz, Germany

[21] Appl. No.: 660,344

[22] Filed: Feb. 23, 1976

[51] Int. Cl.² .................. C07F 7/08; C07F 7/18
[52] U.S. Cl. .................. 260/448.2 E; 260/448.2 Q; 260/448.8 R
[58] Field of Search ............ 260/448.2 E, 448.8 R, 260/448.2 Q

[56] References Cited

U.S. PATENT DOCUMENTS

| | | | |
|---|---|---|---|
| 2,632,013 | 3/1953 | Wagner et al. | 260/448.2 E |
| 2,823,218 | 2/1958 | Speier et al. | 260/448.2 E |
| 3,658,866 | 4/1972 | Tsuji et al. | 260/448.2 E |

OTHER PUBLICATIONS

Speier et al., "J.A.C.S.", 79, 1957, pp. 974–979.

*Primary Examiner*—Paul F. Shaver
*Attorney, Agent, or Firm*—Tab T. Thein

[57] ABSTRACT

Process for preparing 2-(cyclohexenyl-4-)ethyl-silicon compounds from Si compounds containing SiH groups by reacting the latter compounds with vinylcyclohexene-4 in the presence of $H_2PtCl_6$ as addition catalyst at normal pressure and temperatures ranging from 20° to 200° C. The invention also includes novel compounds made by the process. The compounds impart excellent air-drying properties to silicone varnishes and are useful additives in the plastics and casting industries.

7 Claims, No Drawings

PROCESS FOR PREPARING 2-(CYCLOHEXENYL-4-)ETHYL-SILICON COMPOUNDS AND NOVEL PRODUCTS MADE THEREBY

The present invention relates to a process for preparing 2-(cyclohexenyl-4-)ethyl-silicon compounds and novel products made thereby. More particularly the invention relates to preparing 2-(cyclohexenyl-4-)ethyl-silanes and 2-(cyclohexenyl-4-)ethyl-siloxanes by addition of silicon compounds containing SiH groups to vinylcyclohexene-4 in the presence of $H_2PtCl_6$ as catalyst.

It is known that trichlorosilane reacted in an autoclave with vinylcyclohexene-4 at 340° C yields bis-(triclorosilyl)cyclohexene in an output of 21%, see U.S. Pat. No. 2,545,780.

Methyldichlorosilane can be added to vinylcyclohexene-4, with platinum on charcoal as catalyst, at a temperature of 100° to 135° C yielding 81% of 2-(cyclohexenyl-4-)ethyl-methyldichlorosilane. However the reaction proceeds very slowly and requires 23 hours, see Speier et al.: J. Amer. Chem. Soc. 79 (1957) pp. 974-9. It is true that the reaction time may be shortened to 6 hours but this requires operating in an autoclave at 180° C.

The addition product of methyldichlorosilane with vinylchlorohexene-4 is also formed when methyldichlorosilane is added to butadiene in an autoclave, see Petron et al., Isw. Akad. Nauk. USSR, Ochn. (1957) pp. 1206-7.

The further processing of cyclohexenyl-ethyl-Si compounds, primarily polymerization, occurs in the presence of hexachloroplatinic acid; see German patent publication (for opposition) No. 1,069,148.

The above described processes are lengthy, not very specific, and technically complicated, since operating in autoclaves is necessary if reasonable reaction times and satisfactory yields are to be obtained.

The addition of trichlorosilane, triethoxysilane, and of siloxanes containing SiH groups to vinylcyclohexene-4 has not been described up to now.

It is the object of the present invention to provide processes for the preparation of organosilicon compounds, more particularly of specific organosilicon compounds which are simple to operate on an industrial scale and can be carried out continuously.

It is another object of the invention to prepare organofunctional silicon compounds in good yields at practically normal conditions of pressure and temperature.

Other objects and advantages of the invention will become apparent from the following detailed description.

According to the invention it has been found that SiH groups containing silicon compounds are added specifically to the vinyl group of vinylcyclohexene-4 within short reaction times at normal pressure in the presence of hexachloroplatinic acid and that the yields are exceptionally good. Contrary to experiences hitherto made, the double bond of the cyclohexene ring will remain intact.

The following formulas illustrate the reaction:

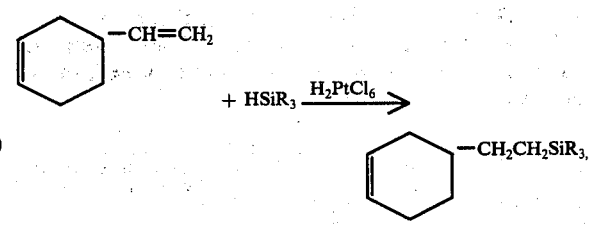

wherein R represents the same or different radicals, such as halogen, alkyl, cycloalkyl, aryl, alkoxy, carboxy or aroxy.

The addition of siloxanes containing SiH groups to vinylcyclohexene-4 has similar good results.

One advantage of the above-mentioned addition reactions consists in the possibility to carry out the operations wiithout autoclaves, by simple heating of the components under reflux, continuously through a heatable column containing filling material. This is one of the few addition reactions which can be carried out continuously due to the simple manipulations.

The 2-(cyclohexenyl-4-)ethyl-silicon compounds made according to the invention impart excellent air-drying properties to silicone varnishes or silicone combination varnishes. They are also very useful additives in various applications of the plastics and casting industries.

In the following the invention will be more fully described in a number of examples but it should be understood that these are given by way of illustration and not of limitation.

EXAMPLE 1

1 mol vinylcyclohexene-4 and 0.1 mol methyldichlorosilane are heated to boiling with 0.5 ml 0.1 m (molar concentration) $H_2PtCl_6$ dissolved in isopropanol. 0.9 mol methyldichlorosilane are added dropwise in such a manner that a good reflux will be caused without heating. After 50 minutes, the sump temperature will reach 160° C and the addition is completed.

Distillation of the reaction mixture results at 96° to 100° C/4 torr in a yield of 171 g (77% of the theoretical) of 2-(cyclohexenyl-4 -)ethyl-methyldichlorosilane showing the following anaylsis values:

| | $n_D^{20}$ | $d_4^{20}$ | BrZ (bromine number) 0.72 grams bromine per grams of substance |
|---|---|---|---|
| Lit. or calc.: | 1.4829 | 1.0771 | |
| Found: | 1.4819 | 1.078 | 0.76 |
| Lit. or calc.: | C | H | Cl |
| | 48.42% | 7.23% | 31.76% |
| Found: | 49 % | 7.3% | 31.7% |

EXAMPLE 2

2 mols triethyoxysilane are heated with 2 mols vinylcyclohexene-4 and 0.1 ml 0.1 m $H_2PtCl_6$ in isopropanol, the temperature rising rapidly, beginning at 80°to 160° C. Further heating of one hour's duration at the temperature completes the addition, but is not absolutely necessary. The addition will occur also without heating of the addition mixture by simply letting it stand at room temperature, but it will take somewhat longer.

Distillation in vacuo at 97° C/0.3 torr results after separation of the first run in a yield of undistilled product 2-(cyclohexenyl-4-)ethyl-triethoxisilane of 499 g (92% of the theoretical) and after distillation at 100° to 107° C/0.3 torr of 485 g (89% of the theoretical).

The addition reaction is so specific that distillation in vacuo may be dispensed with, as will be seen from the elementary analysis below.

| $C_{14}H_{28}O_3Si$ calc.: $n_D^{20}$ | | BrZ 0,.59 grams bromine per grams of substance | |
|---|---|---|---|
| undist. found: | 1.4424 | 0.54 | |
| dist.   " | 1.4422 | 0.54 | |
| $C_{14}H_{28}O_3Si$ calc.: C | 61.71% H | 10.36% Si | 10.31% |
| undist. found: | 62.7 % | 11.2 % | 12.3 % |
| dist.   " | 61.7 % | 10.9 % | 11.2 % |

An increase in the quantity of catalyst to more than 0.05 ml 0.1 m $H_2PtCl_6$ per mol of vinylcyclohexene-4 does not result in an increased yield of the addition product.

EXAMPLE 3

2 mols vinylcyclohexene-4 are heated with 0.2 mol $HSiCl_3$ and 0.1 ml 0.1 m $H_2PtCl_6$, and as soon as reflux sets in, the remaining 1.8 mols trichlorosilane are added dropwise in such a manner that a good reflux will result. The addition is completed within one hour.

The crude product so obtained is slightly yellowish and can be further processed without distillation. Separation of small amounts of first run to 80° C/0.6 torr does not result in essentially improving the quality of the formed 2-(cyclohexenyl-4-)ethyl-trichlorosilane, which is obtained in a yield of 97%.

| $C_8H_{13}Cl_3Si$ calc.: | $d_4^{20}$ | BrZ 0.64 grams bromine per grams of substance | | |
|---|---|---|---|---|
| crude product found: | 1.19 | 0.66 | | |
| first run separ. " | 1.194 | 0.63 | | |
| $C_8H_{13}Cl_3Si$ calc.: | C | H | Si | Cl |
| | 39.44% | 5.38% | 11.53% | 43.65% |
| crude product found: | | | | 44.4 % |
| first run separ. " | 39.96% | 5.5% | 12.4 % | 42.9 % |

EXAMPLE 4

0.5 mol diphenyl-hexamethyl-tetrasiloxane (SiH content 0.475%) are heated with 0.25 ml 0.1 m $H_2PtCl_6$ in isopropanol and 0.5 mol vinylcyclohexene-4. During the reaction, the temperature in the flask rises within 30 minutes to 200° C beyond the temperature in the heating bath which is 142° C.

The crude yield of the addition mixture consisting for the largest part of bis[(cyclohexenyl-4-)ethyl-]-diphenyl-hexamethyl-tetrasiloxane) amounts to 99% since heating in vacuo up to 80° C/0.5 torr does not yield any distillate.

| calc: | BrZ 0.52 grams bromine per grams of substance |
|---|---|
| found: $n_D^{20}$ 1.507 $d_4^{20}$ 1.013 visc. 47 cSt | 0.48 |

EXAMPLE 5

A methylsilicone oil is heated with vinylcyclohexene-4 and $H_2PtCl_6$; the SiH value of the oil is 0.265%, and the following amounts are reacted: 0.64 mol of oil calculated on the SiH value, 0.64 mol of vinylcyclohexene-4 and 0.8 ml 0.1 m $H_2PtCl_6$. During the reaction, the temperature in the flask rises rapidly to 195° C beyond the bath temperature of 100° C. The addition is completed in 1 hour. No first run can be separated up to 80° C/0.5 torr. The cyclohexenylethyl-modified methylsilicone oil no longer contains any SiH group and has the following characteristics:

mol. weight 1278 $n_D^{20}$ 1.432 $d_4^{20}$ 0.972 visc. 59 cSt, BrZ 0.13 grams bromine per grams of substance

EXAMPLE 6

On a heatable column of 2 meters length which contains filling material, the following reactants are introduced within an hour at the top by means of a dropping funnel: 5 mols vinylcyclohexene-4 with 0.25 ml 1 m $H_2PtCl_6$ in isopropanol and 5 mols $HSiCl_3$. The following temperatures are, for instance, prevailing: upper third of the column: room temperature, center third: 75° C, bottom third: 50° C in heating jacket. Time of passage through column: one minute.

Within the column, the mixture heats up to over 120° C due to heat generated by the addition reaction. No further heating is therefore necessary once the reaction has started.

The addition product accumulated in the flask yields upon heating in vacuo up to 120° C/5 torr a first run up to 46° C/5 torr amounting to 43 g (3.5% of the starting material). The undistilled 2-cyclohexenyl-4-)ethyltrichlorosilane obtaihed, 1180 g = 96.5% of the theoretical, has the following characteristics:

| calc.: | Cl | | BrZ 0.64 grams bromine per grams of substance |
|---|---|---|---|
| | 43.65% | | |
| found: | 42.7 % | $n_D^{20}$ 1.4869 $d_4^{20}$ 1.19 | 0.61 |

It should be understood, of course, that the foregoing disclosure relates only to preferred embodiments of the invention, and that it is intended to cover all changes and modifications of the examples described which do not constitute departures from the spirit and scope of the invention.

What we claim is:

1. A process for preparing 2-(cyclohexenyl-4-)ethyl-silicon compounds from Si compounds containing SiH groups, which comprises the steps of reacting the Si compounds in the presence of hexachloroplatinic acid as addition catalyst with vinylcyclohexene-4 at normal pressure and at temperatures between 20° and 200° C.

2. The process as defined in claim 1, wherein 0.0001 to 5 ml 0.1 m (molar concentration) of the hexachloroplatinic acid, dissolved in an organic solvent, is added per mol vinylcyclohexene-4.

3. The process as defined in claim 1, wherein the Si compounds are those of the formula $HSiR_3$, with R standing for radicals being a member of the group consisting of halogen, alkyl, cycloalkyl, aryl, alkoxy, carboxy and aroxy.

4. The process as defined in claim 3, wherein the radicals R in the formula $HSiR_3$ are all the same.

5. The process as defined in claim 3, wherein the radicals R in the formula $HSiR_3$ are different.

6. The process as defined in claim 1, wherein the Si compounds are siloxanes.

7. The processes as defined in claim 1, wherein the reaction is carried out continuously.

* * * * *

UNITED STATES PATENT OFFICE
CERTIFICATE OF CORRECTION

Patent No. 4,038,302  Dated July 26, 1977

Inventor(s) Sigrid Reichel et al.

It is certified that error appears in the above-identified patent and that said Letters Patent are hereby corrected as shown below:

Column 1, line 32, change to read -- 1206 to 1217. --;

column 2, line 39, correct the spelling of "vinylcyclohexene-4";

column 2, line 48, correct the spelling of "2-(cyclohexenyl-4-)ethyl- ...";

column 3, line 3, correct the spelling of "... triethoxysilane";

line 10, correct the spelling of "0.59";

line 60, correct to read
-- found: $n_D^{20}$ 1.507  $d_4^{20}$ 1.013  visc. 47 cSt --;

UNITED STATES PATENT OFFICE
CERTIFICATE OF CORRECTION

Patent No. 4,038,302          Dated July 26, 1977

Inventor(s) Sigrid Reichel et al.

It is certified that error appears in the above-identified patent and that said Letters Patent are hereby corrected as shown below:

column 4, lines 33 to 35, correct in part to read
    -- calc.:      Cl 43.65%
        found:        42.7% --; and column 4, line 63, change "$are\ different.$" to -- are different. --.

Signed and Sealed this

Twenty-eighth Day of March 1978

[SEAL]

Attest:

RUTH C. MASON          LUTRELLE F. PARKER
Attesting Officer       Acting Commissioner of Patents and Trademarks